United States Patent [19]
Anseth et al.

[11] Patent Number: 5,902,599
[45] Date of Patent: *May 11, 1999

[54] BIODEGRADABLE POLYMER NETWORKS FOR USE IN ORTHOPEDIC AND DENTAL APPLICATIONS

[75] Inventors: Kristi S. Anseth, Boston; Robert Langer, Newton; Venkatram R. Shastri, Allston, all of Mass.

[73] Assignee: Massachusetts Institute of Technology, Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/603,171

[22] Filed: Feb. 20, 1996

[51] Int. Cl.$^6$ .............................. A61F 2/28; A61F 2/30; A61K 47/32; C08F 2/46

[52] U.S. Cl. ......................... 424/426; 424/422; 424/427; 424/428; 424/484; 424/486; 424/487; 514/772.6; 522/1; 522/6; 522/33; 522/38; 522/40; 522/43; 522/60; 523/114

[58] Field of Search .................................... 424/426, 427, 424/428, 422, 486, 484, 487; 523/114; 514/772.6; 522/1, 6, 33, 38, 40, 43, 60

[56] References Cited

U.S. PATENT DOCUMENTS

| | | | |
|---|---|---|---|
| 2,073,316 | 3/1937 | Niederl | 260/143 |
| 3,297,033 | 1/1967 | Schmitt et al. | 128/335.5 |
| 3,739,773 | 6/1973 | Schmitt et al. | 128/92 BC |
| 3,839,297 | 10/1974 | Wasseman et al. | 260/78.3 |
| 4,052,988 | 10/1977 | Doddi et al. | 128/335.5 |
| 4,343,931 | 8/1982 | Barrows | 528/291 |
| 4,789,724 | 12/1988 | Domb et al. | 528/176 |
| 4,872,936 | 10/1989 | Engelbrecht | 156/307.3 |
| 4,891,225 | 1/1990 | Langer et al. | 424/428 |
| 4,919,151 | 4/1990 | Grubbs et al. | 128/898 |
| 4,946,929 | 8/1990 | D'Amore et al. | 528/206 |
| 5,011,691 | 4/1991 | Opermann et al. | 424/423 |
| 5,019,379 | 5/1991 | Domb et al. | 424/78 |
| 5,108,755 | 4/1992 | Daniels et al. | 424/426 |
| 5,236,563 | 8/1993 | Loh . | |
| 5,367,002 | 11/1994 | Huang et al. | 523/16 |

FOREIGN PATENT DOCUMENTS

| | | |
|---|---|---|
| 0266603 | 5/1988 | European Pat. Off. . |
| 1034123 | of 0000 | United Kingdom . |
| WO 89/00855 | 2/1989 | WIPO . |
| WO 89/01006 | 2/1989 | WIPO . |

OTHER PUBLICATIONS

Anseth, et al., "Polymeric Dental Composites," *Adv. Polym. Sci,* 122:177–217 (1995).

Hanafusa, et al., "Biodegradable Plate Fixation of Rabbit Femoral Shaft Osteotomies," *Clin, Ortho. Rel. Res.,* 315:261–271 (1995).

Hill–West, et al., "Prevention of Postoperative Adhesions in the Rat by In Situ Photopolymerization of Bioresorbable Hydrogel Barriers," *Obstet. Gynecol.,* 83:59–64 (1994).

Conix, "Polly[1,3–bis(p–carboxphenoxy)–propane anhydride]," *Macromol. Synth.,* 2:95–99 (1966).

Ruyter and Ovsaed, "Analysis And characterization of Dental Polymers," *CRC Crit. Rev. Biocomp.,* 4:247–279 (1988).

Leong, et al., "Bioerodible Polyanhydides As Drug–Carrier Matrices. I: Characterization, Degradation, and Release Characteristics," *J. Biomed. Mater. Res.,* 19:941–955 (1985).

Uhrich, et al., "Synthesis and Caracterization of Degradable Poly(anhydride–co–imides)," *Macromolecules* 28:2184–2193 (1995).

Pulapura and Kohn, "Trends in the Development of Bioresorbable Polymers for Medical Applications," *J. Biomater. Appl.,* 6:216–250 (1992).

*Primary Examiner*—Lynette F. Smith
*Assistant Examiner*—M. K. Zeman
*Attorney, Agent, or Firm*—Arnall Golden & Gregory, LLP

[57] ABSTRACT

Biodegradable polymer networks are provided which are useful in a variety of dental and orthopedic applications. The biodegradable polymer networks can be formed in one embodiment by polymerizing anhydride prepolymers including crosslinkable groups, such as unsaturated moieties. The anhydride prepolymers can be crosslinked, for example in a photopolymerization reaction by irradiation of the prepolymer with light in the presence of a free radical initiator. Suitable anhydride prepolymers include dianhydrides of a dicarboxylic acid and a carboxylic acid molecule comprising a crosslinkable group. For example, methacrylic acid dianhydrides of monomers or oligomers of a diacid such as sebacic acid or 1,3-bis(p-carboxyphenoxy)-hexane can be used. The anhydride prepolymers can be applied in vivo to a site where an orthopedic implant is needed, and then may be crosslinked, for example, by irradiation with U.V. light, to form a biodegradable implant such as a rods, pin or plate. The implants advantageously provide mechanical support and also are capable of slow surface degradation to permit bone ingrowth.

32 Claims, No Drawings

BIODEGRADABLE POLYMER NETWORKS FOR USE IN ORTHOPEDIC AND DENTAL APPLICATIONS

This invention was sponsored in part by the National Institutes of Health through a fellowship to Kristi S. Anseth and NIH Grant No. AR41972. The government has certain rights in the invention.

The present invention relates generally to methods for crosslinking anhydride monomers or oligomers to form biodegradable, crosslinked polymer networks for use in orthopedic and dental applications.

A variety of different orthopedic and dental implants have been developed. Metallic orthopedic devices, have been fabricated, however these devices shield stress during healing and can lead to bone atrophy. Hanafusa et al., *Clin. Ortho. Rel. Res.*, 315:261 (1995). Poly(methyl methacrylate) (PMMA) is a polymer which is widely used in current bone cement systems. The material is molded prior to implantation as it is polymerizing which allows a limited "window" of processing time. While the physical and mechanical properties of PMMA are appropriate for load-bearing applications the material is non-degradable which can hinder healing.

The manufacture of absorbable orthopaedic devices from a variety of different materials has been described, e.g.: sutures and surgical elements made from polyglycolide (U.S. Pat. No. 3,297,033 and U.S. Pat. No. 3,739,773) sutures from polylactide (U.S. Pat. No. 2,703,316), sutures from glycolide/lactide copolymers (U.S. Pat. No. 3,839,297), sutures and osteosynthesis devices from poly-β-hydroxybutyric acid (G.B. Pat. No. 1 034 123), sutures and osteosynthesis devices from polydioxanone (U.S. Pat. No. 4,052,988), and surgical devices from polyesteramides (U.S. Pat. No. 4,343,931). These devices typically are plates which are fixed to bone by screws, cylindrical nails, or corresponding structures manufactured by melting, molding, or pressing the polymer into the desired form. Typically, the tensile strengths of the unhydrolyzed samples are between 40–80 MPa which is modest compared to the strength of cortical bone (about 80 to 200 MPa). In addition, many of these systems are either too brittle or flexible to be used in many bone surgical applications. Thus, the existing applications of resorbable polymers in orthopaedic surgery have been limited because of difficulties associated with processing and the physicomechanical properties of the polymers.

Degradable polyesters such poly (L-lactic acid), poly (glycolic acid), and poly(lactic-co-glycolic acid) are approved for human use by the Food and Drug Administration, and have been used in many medical applications, for example, in sutures. These polymers, however, lack many properties necessary for restoring function in high load-bearing bone applications, since they undergo homogeneous, bulk degradation which is detrimental to the long-term mechanical properties of the material and leads to a large burst of acid products near the end of degradation. In contrast, surface eroding polymers (such as polyanhydrides) maintain their mechanical integrity by preserving the molecular weight of the polymer and exhibit a gradual loss in size which permits bone ingrowth. However, current linear polyanhydride systems have limited mechanical strength.

Photopolymerizable systems have been developed for use in dentistry. Anseth et al., *Adv. Polym. Sci*, 122:177 (1995); U.S. Pat. No. 4,872,936 to Engelbrecht; and U.S. Pat. No. 5,367,002. In dentistry, methacrylate-based resins are photocured to produce restorative materials, however, these materials are nondegradable and permanent. Synthetic photopolymerizable systems also have been used in opthamology (e.g., U.S. Pat. No. 4,919,151 to Grubbs et al.). Synthetic photopolymerizable systems have been developed to replace the lens in the eye, after cataract formation, consisting of a polyether with urethane linkages end-capped with acrylate, methacrylate, or styrene. As in the dental applications, the photopolymerized polymer is a permanent and nondegrading system. Photopolymerizable systems have also been used in adhesion prevention (Hill-West et al., *Obstet. Gynecol.*, 83:59 (1994)). In adhesion prevention, degradable and photopolymerizable hydrophilic oligomers of poly(ethylene glycol) end-capped with lactic acid and acrylate functionalities have been developed. While degradable, these systems are hydrogels of limited mechanical strength and degrade on a relatively short timescale.

There is a need for biodegradable polymers which can be used in dental and orthopedic applications. There also is a need for methods for forming polymeric implants which provide mechanical strength but which also are biodegradable in vivo. There further is a need for biodegradable polymers which can be polymerized in vivo, and which can be readily implanted and shaped for a particular application.

It is therefore an object of the present invention to develop biodegradable polymers which have optimal mechanical properties, particularly as the polymer degrades, for orthopaedic applications. It is a further object of the invention to develop crosslinkable prepolymers which rapidly polymerize at a room temperature, which can be used to form polymerized biodegradable implants with varying different geometries. It is still another object of the invention to provide biodegradable polymers for use in dental and orthopedic applications which biodegrade in vivo at a rate which can be determined by the composition and degree of crosslinking of the polymer.

SUMMARY OF THE INVENTION

Biodegradable polymer networks are provided which are useful in a variety of dental and orthopedic applications. The biodegradable polymer networks can be formed in one embodiment by polymerizing anhydride prepolymers including crosslinkable groups, such as unsaturated moieties. The anhydride prepolymers can be crosslinked, for example in a photopolymerization reaction by irradiation of the prepolymer with light in the presence of a free radical initiator. Suitable anhydride prepolymers include dianhydrides of a dicarboxylic acid and a carboxylic acid molecule comprising a crosslinkable group. For example, methacrylic acid dianhydrides of monomers or oligomers of a diacid such as sebacic acid or 1,6-bis(p-carboxyphenoxy)-hexane can be used. In one embodiment, the anhydride prepolymers can be applied in vivo to a site where an orthopedic implant is needed, and then may be crosslinked, for example, by irradiation with ultraviolet light, to form a biodegradable implant. The implants advantageously provide mechanical support and also are capable of slow surface degradation to permit bone ingrowth.

DETAILED DESCRIPTION OF THE INVENTION

Crosslinkable anhydride monomers or oligomers are provided which are capable of reacting to form highly crosslinked, biodegradable polyanhydride networks, which are useful in a variety of different biomedical applications. In one embodiment, the anhydride monomers or oligomers may be crosslinked by radiation-induced polymerization, for example, by photopolymerization. The high degree of crosslinking produces polymers with enhanced mechanical properties. The crosslinked polymers are capable of surface controlled degradation under in vivo conditions. The rate of degradation can be controlled by selection of the polymer network composition and the crosslinking density within the polymer network. In one embodiment, the crosslinked polymers can be formed in vivo by the photopolymerization of anhydride monomers or oligomers, and may be designed and shaped as required for a variety of different orthopedic and dental applications.

Crosslinkable Anhydride Monomers and Oligomers

Biodegradable crosslinked polymer networks are formed by crosslinking functionalized anhydride monomers or oligomers. Useful functionalized monomers or oligomers include mixed anhydrides of a diacid and a carboxylic acid molecule which includes a crosslinkable group such as an unsaturated moiety. Exemplary anhydride monomers or oligomers include mixed anhydrides of diacids, such as sebacic acid or 1,6-bis(p-carboxyphenoxy)-hexane (MCPH), and a carboxylic acid including an unsaturated moiety such as methacrylic acid. The functionalized anhydride monomers or oligomers are formed, for example, by reacting the diacid with an activated form of the acid, such as an anhydride thereof, to form a mixed anhydride.

Other dicarboxylic acids, or multifunctional acids, or mixtures thereof, can be used, such as dodecanedioic acid, fumaric acid, bis(p-carboxyphenoxy)methane, 1,6-bis(p-carboxyphenoxy)propane, terephthalic acid, isophthalic acid, p-carboxyphenoxy acetic acid, p-carboxyphenoxy valeric acid, p-carboxyphenoxy octanoic acid, or citric acid, which are capable of being functionalized by forming mixed anhydrides with a carboxylic acid comprising a crosslinkable group. The carboxylic acid molecule including a crosslinkable group, in the functionalized prepolymer, can be, for example, a carboxylic acid including an unsaturated moiety, such as methacrylic acid, or other functionalized carboxylic acids, including, e.g., acrylic, methacrylic, vinyl and/or styryl groups.

Preferably, the crosslinkable groups are photopolymerizable groups, such as alkenes, which may be polymerized in a free radical reaction upon irradiation with light in the presence of an initiator. Crosslinkable groups include, for example, acrylates, diacrylates, oligoacrylates, methacrylates, dimethacrylates, oligomethoacrylates, or other biologically acceptable photopolymerizable groups. The functionalized anhydride prepolymers thus in one embodiment may be in the form of a linear anhydride with a crosslinkable unsaturated moiety at each terminus of the the linear anhydride.

The resulting prepolymers, consisting of functionalized anhydride monomers and oligomers, including crosslinkable groups such as unsaturated moieties, can be crosslinked, for example, in a photopolymerization reaction to produce highly crosslinked biodegradable polymer networks. The hydrolyzable anhydride linkages make the material biodegradable, and the rate of degradation readily can be controlled by changes in the network composition and the crosslinking density.

As used herein the term "biodegradable" refers to the ability of a material to degrade in the body by being broken down by processes such as hydrolysis or metabolic degradation.

Crosslinking of Functionalized Monomers

An example of the synthesis of the mixed anhydride functionalized monomers, and the subsequent crosslinking of the monomers to form a crosslinked polymer network is shown in Scheme 1. In this embodiment, functionalized monomers (and oligomers) of sebacic acid (MSA) and 1,6-bis(p-carboxyphenoxy)-hexane (MCPH) were synthesized and polymerized. First the dicarboxylic acid monomers were converted to their mixed anhydride with methacrylic anhydride by heating at reflux.

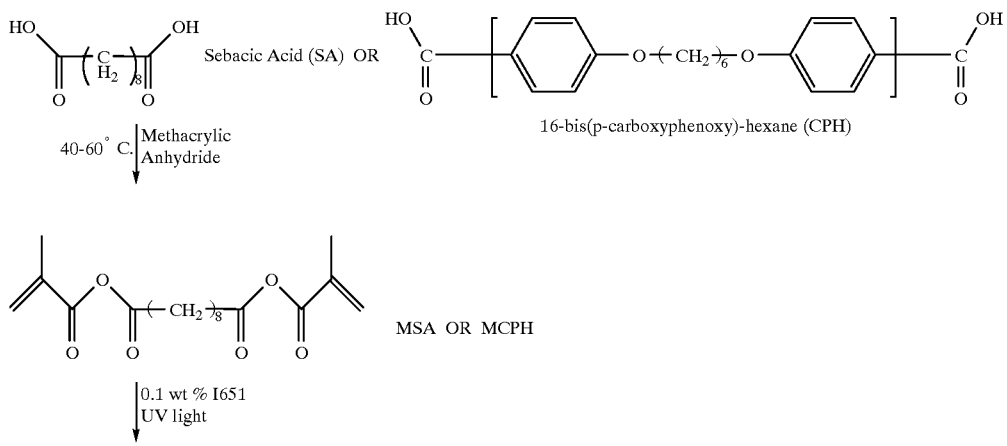

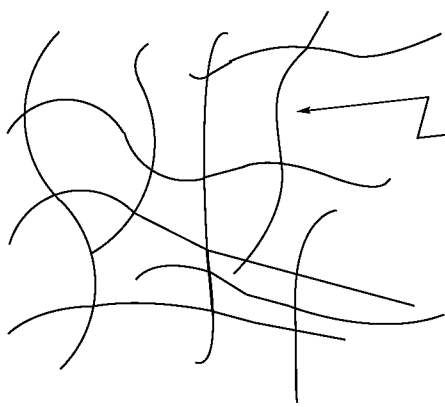
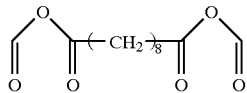

Crosslinked Network of Poly(MSA)

The functionalized monomeric or oligomeric prepolymers were isolated and purified by vacuum distillation or by dissolving in methylene chloride and precipitation from diethyl ether.

In the illustrative embodiment shown in Scheme I, photopolymerization was initiated with 0.1 wt % of 2,2-dimethoxy-2-phenylacetophenone dissolved in each monomer and ultraviolet light of varying intensity (0.1 mW/cm$^2$ to 1000 mW/cm$^2$). The high concentration of double bonds in the system and the multifunctional nature of the monomer (two double bonds per monomer molecules) causes the formation of a highly crosslinked polymer system in a period of a few seconds, depending on the initiation rate.

Fourier-transform infrared spectroscopy (FTIR) and differential scanning photocalorimetry (DPC) can be used to characterize the polymerization behavior, curing time, and maximum double bond conversion in these systems. In systems for orthopedic applications, both the polymerization time and maximum conversion are critical factors with desirable systems polymerizing in less than one minute and approaching 100% conversion of their functional groups.

The crosslinking density and the hydrophilicity of the crosslinked biodegradable polymers may be altered by copolymerizing the diacid, such as MSA and MCPH, in various proportions. For example, MSA may be used to increase the hydrophilicity of the resulting network, while MCPH may be used to increase the hydrophobicity. The polymerization conditions, including polymer composition and crosslinking density, polymerization time, and light intensity, may be optimized for a particular application. In particular, the monomers and reagents can be selected in order to optimize the degradation characteristics of the polymer and the material strength.

The mechanical properties of the highly crosslinked materials are significantly improved in the tensile modulus as compared to existing degradable materials. The crosslinkable systems provide not only great flexibility in processing, but also enhanced mechanical properties of the resulting polymer.

Crosslinking Agents

In a preferred embodiment, crosslinking groups are crosslinked by radiation-induced polymerization, for example, by irradiation with light. In one embodiment, the crosslinking groups can be crosslinked by irradiation with ultraviolet or visible light at a wavelength of between about 250 and 700 nm. For example, ultraviolet light at a wavelength of about 365 nm, or red visible light at a wavelength of about 642 nm, or blue visible light at a wavelength of between 470 and 490 nm may be used. The use of blue light at a wavelength of between 470 and 490 nm is useful for dental applications. Additionally, electron beams, x-rays, γ-rays and other forms of radiation may be used to initiate polymerization of prepolymers.

Biocompatible photoinitiators can be used to initiate free radical polymerization of the prepolymers within a short time frame, minutes at most and most preferably seconds. Exemplary photoinitiators include Irgacure 651™ (2,2-dimethoxy-2-phenylacetophenone), dyes such as eosin dye, and initiators such as 2,2-dimethyl-2-phenylacetophenone, 2-methoxy-2-phenylacetophenone, and camphorquinon. Other free radical initiators include, e.g., an α-diketone, a tertiary amine, a tertiary phosphine, an organic peroxide, peroxides in combination with a reducing agent, aliphatic and aromatic ketones, benzoin, benzoin ethers, benzil and benzil ketals, or combinations thereof. For example, benzophenone or acetophone can be used. Using such initiators, prepolymers may be polymerized in situ, for example, by long wavelength ultraviolet light or by focused laser light.

Thermal polymerization initiator systems also may be used, which can initiate free radical polymerization at physiological temperatures including, for example, potassium persulfate, benzoylperoxide, and ammonium persulfate. Additionally, ionic initiators, including cationic initiators may be used.

The prepolymers can be applied in vivo and then reagents, such as light curing agents, or other initiating systems, such as thermal and redox systems can be applied, or the prepolymers can be combined with crosslinking agents or fillers prior to in vivo application.

In Vivo Applications

The biodegradable crosslinked polymers can be used in a variety of biomedical applications, including musculoskeletal and dental applications. The biodegradable polymers are biocompatible, strong, easily fashioned, and degradable, and can be polymerized in vivo to allow easy placement and fabrication. The polymers degrade at a controlled rate depending on the composition and crosslinking of the polymer, eliminating the need for retrieval.

In orthopedic applications, in situ polymerization eliminates the need for shaping the implant with blades, burrs, and warming instruments. Additionally, the process provides a faster and better mechanism for fabricating complex geometries and improves adhesion of the polymer implant to the bone. Photoinitiated polymerizations allow spatial control of the polymerization so that complex patterns can be produced using lasers to produce desired shapes. In addition, the materials can be injection molded and reacted as a thermoset to produce desired shapes from molds ex vivo. The materials can be used in many applications requiring load-bearing capacities and controlled degradation. In a preferred embodiment, the compression modulus of the polymers is on the order of about 100 MPa to about 20,000 MPa.

The biodegradable networks permit treatment of bone fractures through fixation since the crosslinked polymers provide sufficient strength to permit fixation, good tissue/material compatibility, and facile molding (into potentially complex shapes) for easy placement. In addition, controlled degradation of the polymers permits optimum bone function upon healing. The materials can reestablish the mechanical integrity of the bone and subsequently degrade to allow new bone formation to bear load and remodel. These properties are a major advantage of the degradable polymeric materials over metallic orthopedic devices which shield stress during healing and can lead to bone atrophy. The biodegradable polymer networks disclosed herein, in contrast, are surface eroding polymers (controlled by hydrophobicity and/or crosslinking density) which maintain their mechanical integrity and undergo a gradual loss in size which permits bone ingrowth.

In the embodiment wherein photopolymerizable functionalized anhydride monomers or oligomers are used, the use of photoinitiation to crosslink the prepolymers greatly simplifies the clinical insertion of orthopaedic polymer implants. For example, in pin applications, a viscous, liquid monomer may be introduced into a pin hole and the system photopolymerized in situ to render a hardened polymer of the required dimensions. Photopolymerizable systems are beneficial for many reasons including fast curing rates at room temperature, spatial control of the polymerization, and complete ease of fashioning and flexibility during implantation. The use of photopolymerizable orthopaedic implants provides a broad range of systems which can be designed for a particular surgical application. Degradable polymeric implants also eliminate the need for implant retrieval and can be used simultaneously to deliver therapeutic drugs.

The anhydride prepolymers can be applied to the site in the body of an animal where an implant is needed and then polymerized, or may be polymerized prior to in vivo application, to provide shaped implants within the body which can serve a mechanical function, including, without limitation, rods, pins, screws, and plates. The prepolymers and/or initiating agents can be provided in combination with a pharmaceutically acceptable carrier for implantation.

The prepolymers can be combined with fillers, reinforcement materials, radioimaging materials, excipients or other materials as needed for a particular implant application. Examples of fillers include calcium-sodium-metaphosphate which is described in U.S. Pat. No. 5,108,755, the disclosure of which is incorporated herein by reference.

Drug Delivery

The polymerizable functionalized anhydride monomers and/or oligomers optionally can be provided in combination with other degradable or nondegradable polymers, fillers and/or drugs, either before or after polymerization.

The crosslinked biodegradable polymers may be used to deliver therapeutic or diagnostic agents in vivo. Examples of drugs which can be incorporated into the prepolymers and in the resulting crosslinked polymers include proteins, carbohydrates, nucleic acids, and inorganic and organic biologically active molecules. Specific examples include enzymes, antibiotics, antineoplastic agents, local anesthetics, hormones, antiangiogenic agents, antibodies, neurotransmitters, psychoactive drugs, drugs affecting reproductive organs, and oligonucleotides such as antisense oligonucleotides. In orthopedic applications, bone regenerating molecules, seeding cells, and/or tissue can be incorporated into the prepolymer prior to or after polymerization, or may be applied prior to or after formation of the implant at the site of implantation. For example bone morphogenic proteins such as those described in U.S. Pat. No. 5,011,691, the disclosure of which is incorporated herein by reference, can be used in these applications.

The present invention will be further understood by reference to the following non-limiting examples. In the examples, the following materials and methods were used.

Materials

Sebacic acid (SA) and methacrylic anhydride (MA) were used as received from Aldrich, and 1,6-bis(carboxyphenoxy) hexane (CPH) was synthesized as described in Conix, *Macromol. Synth.*, 2:95 (1966). Photopolymerizations were initiated with 0.1 wt % Irgacure® 651 (I651, Ciba Geigy).

Methods

Infrared spectroscopy (Nicolet Magna 550 FTIR), $^1$H NMR (Nicolet 360 MHz), and gel permeation chromatography (Perkin-Elmer, isocratic LC pump 250, oven 101, and LC-30 RI detector at 254 nm) were used to characterize reaction products during the functionalization of the diacid monomers. Differential scanning photocalorimetry (Perkin-Elmer DSC7) and infrared spectroscopy were used to monitor the cure behavior of the functionalized monomers. Samples were polymerized with an ultraviolet-visible light curing system (EFOS, Ultracure (1OOSS) at varying light intensities. Mechanical properties of the resulting polymers were measured using a dynamic mechanical analyzer (Perkin-Elmer, DMA7) and degradation rates were characterized by mass loss.

EXAMPLE 1

Preparation and Photopolymerization of Monomers

Functionalized monomers (and oligomers) of sebacic acid (MSA) and 1,3-bis(p-carboxyphenoxy)-hexane (MCPH) were synthesized and subsequently polymerized as illustrated in Scheme 1. First the dicarboxylic acid monomers were converted to their mixed anhydride with methacrylic anhydride by heating at reflux. The functionalized monomer was isolated and purified by vacuum distillation, or by dissolving in methylene chloride and precipitation from diethyl ether. Photopolymerizations were initiated with 0.1 wt % of I651 dissolved in each monomer and ultraviolet light of varying intensity (0.1 mW/cm$^2$ to 1000 mW/cm$^2$). The high concentration of double bonds in the system and the multifunctional nature of the monomer (two double bonds per monomer molecules) led to the formation of a highly crosslinked polymer system in a period of a few seconds, depending on the initiation rate.

Both Fourier-transform infrared spectroscopy (FTIR) and differential scanning photocalorimetry (DPC) were used to characterize the polymerization behavior, curing time, and maximum double bond conversion in these systems. In the FTIR spectrum for the polymerization of MSA with 0.1 wt % I651 and approximately 50 mW/cm$^2$ of UV light, the methacrylate double bond exhibited a sharp and distinct absorbance near 1640 cm$^{-1}$ from which the total double bond conversion could be calculated. After 10 seconds of exposure, the system reached nearly 45% conversion of its functional groups. With continued irradiation, the double bond absorbance further decreased until a maximum double bond conversion of 94% was reached. Attainment of a maximum double bond conversion in highly crosslinked polymers has been previously reported (Ruyter and Oysaed, *CRC Crit. Rev. Biocomp*, 4:247 (1988)) and results from severe restrictions on the mobility of the reacting species. Thus, these systems are useful in orthopedic applications, where both the polymerization time and maximum conversion are critical factors, and wherein desirable systems polymerize less than 1 minute and approach 100% conversion of their functional groups.

In addition, the crosslinking density and the hydrophilicity of the polymer were altered by copolymerizing MSA and MCPH in various proportions. MSA was used to increase the hydrophilicity of the resulting network while MCPH increased the hydrophobicity. The polymerization method (including copolymer composition and crosslinking density, polymerization time, and light intensity) can be readily optimized for a particular application, to optimize the degradation characteristics of the polymer and the material strength.

EXAMPLE 2

Evaluation of the Mechanical Properties of the Crosslinked Biodegradable Polymers The highly crosslinked materials made as described in Example 1 had significant improvements in the tensile modulus as compared to existing degradable materials. Table 1 provides a comparison of mechanical properties of bone (Yaszemski, Ph.D. Thesis, Massachusetts Institute of Technology, 1995) with that of the crosslinked polyanhydrides.

TABLE 1

Comparison of Material Properties.

| Material | Modulus | | |
|---|---|---|---|
| | Longitudinal | Compression | Shear |
| Cortical Bone | 17–20 GPa | 17–20 GPa | 3 GPa |
| Trabecular Bone | 50–100 MPa* | 50–100 MPa | |
| poly(MSA) | 1 GPa | | 2 GPa |
| poly(MCPH) | 500 MPa | | 900 MPa |

*depends strongly on the density which varies from 0.1 to 1.0 g/cm$^3$

There was a significant increase in the modulus of functionalized and crosslinked poly(MCPH) (500 MPa) as compared to linear CPH (1.3 MPa). Leong et al., *J. Biomed. Mater. Res.*, 19:941 (1985). Other approaches to increasing the mechanical strength of linear polyanhydrides have focused on incorporating imide groups into the polymer backbone. The most promising materials in this class have shown compression strengths of 36–56 MPa (Uhrich et al., *Macromolecules* 28:2184 (1995)), but do not approach the strengths seen with the crosslinked materials. Finally, resorbable sutures of poly(lactic acid) have initial compression yield stresses of 50–60 MPa, but the efficacy in many orthopedic applications is further limited by bulk degradation that occurs on a relatively short time interval, compared to the polyanhydrides. Pulapura and Kohn, *J. Biomater. Appl.*, 6:216 (1992). Thus, the photopolymerizable and crosslinkable systems provide not only great flexibility in processing, but also enhanced mechanical properties of the resulting polymer.

Modifications and variations of the present invention will be obvious to those skilled in the art from the foregoing detailed description. Such modifications and variations are intended to come within the scope of the following claims.

What is claimed is:

1. A method for making biodegradable polymer networks, the method comprising:
   a) providing anhydride prepolymers which comprise mixed anhydrides of
      i) a monomer or oligomer of a diacid or multifunctional acid and
      ii) a carboxylic acid molecule which includes a crosslinkable group, wherein the crosslinkable group is an unsaturated hydrocarbon moiety and wherein the prepolymers are linear with an unsaturated hydrocarbon moiety at each terminus; and
   b) crosslinking the unsaturated moieties in the anhydride prepolymers, to form a crosslinked biodegradable polymer network.

2. The method of claim 1 wherein, in step b), the anhydride prepolymers are crosslinked by a photopolymerization.

3. The method of claim 2 wherein the photopolymerization is initiated by irradiation of the prepolymers with light in the presence of an initiator.

4. The method of claim 3 wherein the prepolymers are irradiated with ultraviolet light.

5. The method of claim 3 wherein the initiator is selected from the group consisting of an α-diketone, a tertiary amine, a tertiary phosphine, an organic peroxide, peroxides in combination with a reducing agent, aliphatic ketones, aromatic ketones, benzoin, benzoin ethers, benzil, benzil ketals, and combinations thereof.

6. The method of claim 1 wherein the anhydride prepolymer comprises a dianhydride of a dicarboxylic acid and a carboxylic acid molecule comprising an unsaturated hydrocarbon moiety.

7. The method of claim 6 wherein the dicarboxylic acid comprises a dicarboxylic acid mixture.

8. The method of claim 6 wherein the anhydride prepolymer comprises a methacrylic acid dianhydride of a monomer or oligomer of a diacid selected from the group consisting of sebacic acid and 1,6-bis(p-carboxyphenoxy)-hexane.

9. A method for forming a biodegradable implant in vivo comprising:
   a) applying to a site in the body of a mammal where an implant is needed in vivo anhydride prepolymers, wherein the anhydride prepolymers comprise mixed anhydrides of
      i) a monomer or oligomer of a diacid or multifunctional acid and
      ii) a carboxylic acid molecule which includes a crosslinkable group, wherein the crosslinkable group is an unsaturated hydrocarbon moiety and wherein the prepolymers are linear with an unsaturated hydrocarbon moiety at each terminus; and
   b) crosslinking the unsaturated moieties in the anhydride prepolymers, to form a crosslinked biodegradable polymer network in the form of an implant at the site.

10. The method of claim 9 wherein, in step b), the anhydride prepolymers are crosslinked by photopolymerization.

11. The method of claim 10 wherein the photopolymerization is initiated by irradiation of the prepolymers with light in the presence of an initiator.

12. The method of claim 11 wherein the initiator is applied in combination with the prepolymers in step a).

13. The method of claim 12 wherein the initiator is selected from the group consisting of an α-diketone, a tertiary amine, a tertiary phosphine, an organic peroxide, peroxides in combination with a reducing agent, aliphatic ketones, aromatic ketones, benzoin, benzoin ethers, benzil, benzil ketals, and combinations thereof.

14. The method of claim 11 wherein the prepolymers are irradiated with ultraviolet light.

15. The method of claim 9 wherein the anhydride prepolymer comprises a dianhydride of a dicarboxylic acid and a carboxylic acid molecule comprising an unsaturated hydrocarbon moiety.

16. The method of claim 9 wherein the anhydride prepolymer comprises a methacrylic acid dianhydride of a monomer or oligomer of a diacid selected from the group consisting of sebacic acid and 1,6-bis(p-carboxyphenoxy)-hexane.

17. The method of claim 9 wherein the implant is selected from the group consisting of an orthopedic and a dental implant.

18. The method of claim 9 wherein the implant comprises an orthopedic implant selected from the group consisting of rods, pins, screws, and plates.

19. A method for forming a biodegradable implant comprising photopolymerizing anhydride prepolymers comprising mixed anhydrides of i) a monomer or oligomer of a diacid or multifunctional acid and ii) a carboxylic acid molecule which includes a crosslinkable group, wherein the crosslinkable group is an unsaturated hydrocarbon moiety and wherein the prepolymers are linear with an unsaturated hydrocarbon moiety at each terminus, to form a crosslinked biodegradable polymer network in the form of an implant, wherein the photopolymerization crosslinks the unsaturated moieties in the prepolymers.

20. The method of claim 19 wherein the anhydride prepolymers comprise dianhydrides of a dicarboxylic acid, and a carboxylic acid molecule comprising a crosslinkable unsaturated moiety.

21. The method of claim 19 wherein the anhydride prepolymer comprises a methacrylic acid dianhydride of a monomer or oligomer of a diacid selected from the group consisting of sebacic acid and 1,6-bis(p-carboxyphenoxy)-hexane.

22. A composition for forming a biocompatible, biodegradable polymeric implant, the composition comprising anhydride prepolymers in combination with a pharmaceutically acceptable carrier, wherein the anhydride prepolymers comprise mixed anhydrides of i) a monomer or oligomer of a diacid or multifunctional acid and ii) a carboxylic acid molecule which includes a crosslinkable group, wherein the crosslinkable group is an unsaturated hydrocarbon moiety and wherein the prepolymers are linear with an unsaturated hydrocarbon moiety at each terminus.

23. The composition of claim 22 wherein the composition further comprises an initiator selected from the group consisting of a free radical initiator and an ionic initiator.

24. The composition of claim 23 wherein the initiator is selected from the group consisting of an α-diketone, a tertiary amine, a tertiary phosphine, an organic peroxide, peroxides in combination with a reducing agent, aliphatic ketones, aromatic ketones, benzoin, benzoin ethers, benzil, benzil ketals, and combinations thereof.

25. The composition of claim 22 wherein the anhydride prepolymer comprises a dianhydride of a dicarboxylic acid monomer or oligomer and a carboxylic acid molecule comprising an unsaturated moiety.

26. The composition of claim 25 wherein the anhydride prepolymer comprises a methacrylic acid dianhydride of a monomer or oligomer of a diacid selected from the group consisting of sebacic acid and 1,6-bis(p-carboxyphenoxy)-hexane.

27. The composition of claim 22 further comprising a therapeutic agent or a diagnostic agent.

28. A biodegradable implant comprising a crosslinked biodegradable polymer network formed by crosslinking anhydride prepolymers, wherein the anhydride prepolymers comprise mixed anhydrides of i) a monomer or oligomer of a diacid or multifunctional acid and ii) a carboxylic acid molecule which includes a crosslinkable group, wherein the crosslinkable group is an unsaturated hydrocarbon moiety and wherein the prepolymers are linear with an unsaturated hydrocarbon moiety at each terminus, and wherein the crosslinking involves the crosslinking of the unsaturated moieties in the prepolymers.

29. The biodegradable implant of claim 28 wherein the anhydride prepolymer comprises a dianhydride of a dicarboxylic acid monomer or oligomer and a carboxylic acid molecule comprising a crosslinkable group.

30. The biodegradable implant of claim 28 wherein the anhydride prepolymer comprises a methacrylic acid dianhydride of a monomer or oligomer of a diacid selected from the group consisting of sebacic acid and 1,6-bis(p-carboxyphenoxy)-hexane.

31. The method of claim 6, wherein the dicarboxylic acid is selected from the group consisting of sebacic acid, dodecanedioic acid, fumaric acid, bis(p-carboxyphenoxy) methane, 1,6-bis(p-carboxyphenoxy)propane, terephthalic acid, isophthalic acid, p-carboxyphenoxy acetic acid, p-carboxyphenoxy valeric acid, p-carboxyphenoxy octanoic acid, and citric acid.

32. The method of claim 1, wherein the carboxylic acid molecule comprising a crosslinkable group is a carboxylic acid including an unsaturated moiety selected from the group consisting of acrylic, methacrylic, vinyl and styryl.

* * * * *